US00PP15490P3

(12) United States Plant Patent
Handy

(10) Patent No.: US PP15,490 P3
(45) Date of Patent: Jan. 25, 2005

(54) ***FOTHERGILLA MAJOR* PLANT NAMED 'BLUE SHADOW'**

(50) Latin Name: *Fothergilla major*
Varietal Denomination: Blue Shadow

(76) Inventor: Gary Handy, 42512 SE. Trubel, Sandy, OR (US) 97055

( * ) Notice: Subject to any disclaimer, the term of this patent is extended or adjusted under 35 U.S.C. 154(b) by 0 days.

(21) Appl. No.: 10/288,680

(22) Filed: Nov. 4, 2002

(65) Prior Publication Data

US 2004/0088770 P1 May 6, 2004

(51) Int. Cl.[7] ..... A01H 5/00
(52) U.S. Cl. ..... Plt./226
(58) Field of Search ..... Plt./226

*Primary Examiner*—Howard J. Locker
(74) *Attorney, Agent, or Firm*—Klarquist Sparkman LLP

(57) ABSTRACT

A new and distinct cultivar of *Fothergilla major* plant characterized by its striking glaucous, blue green leaf color.

2 Drawing Sheets

Botanical classification: *Fothergilla major.*
Cultivar name: 'Blue Shadow'.

The present invention relates to a new and distinct cultivar of deciduous shrub of the genus and species, *Fothergilla major,* and given the cultivar name 'Blue Shadow'. The genus *Fothergilla* is of the family Hamamelidaceae.

The new cultivar was found in a cultivated area by Gary Handy as a basal shoot mutation (bud sport) from a young plant of *Fothergilla major* 'Mt. Airy', an unpatented plant.

*Fothergilla major,* is one of two species of *Fothergilla* native to southeastern USA. These deciduous shrubs are grown for their spring flowers and outstanding autumn foliage color. *Fothergilla major,* or Mountain Witch Hazel, as described in Botanica, The Illustrated A to Z of over 10,000 Garden Plants, is "the best known of the genus and grows to 1.8 to 3 m tall and nearly as wide. Fragrant, white, puffball flowers appear in spring and again in autumn. The dark green leaves, slightly blue beneath, turn vibrant yellows, oranges and reds in the fall."

This new cultivar is characterized by the following:

1. Unique, glaucous blue green leaves.
2. Rounder leaves than parent.
3. Good fall color.
4. Excellent vigor.

Asexual propagation by cuttings in Boring, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
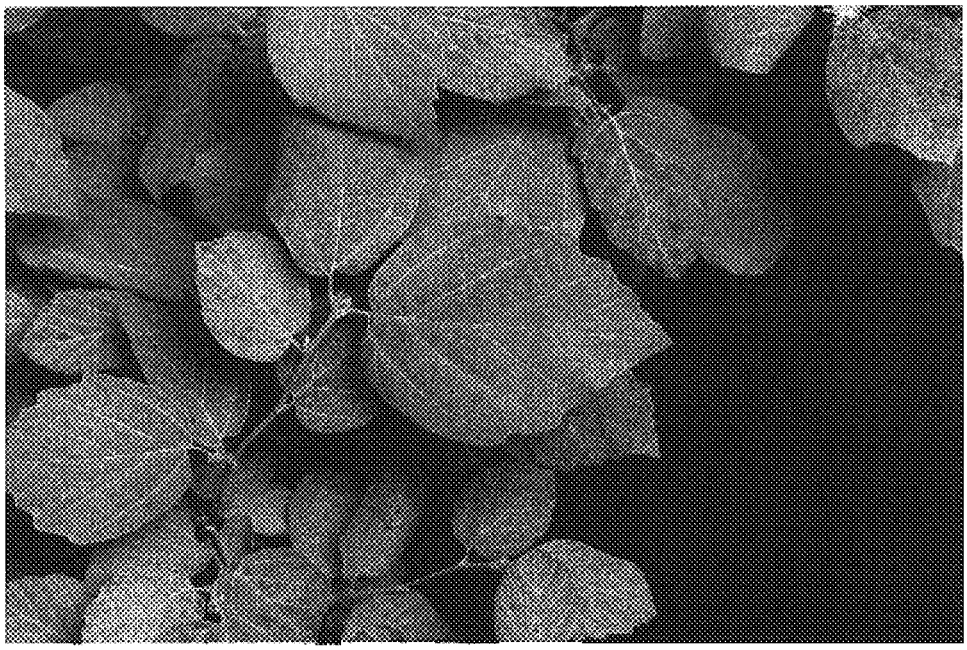
FIG. 1 shows a close up of the new cultivar.
Figure 2:
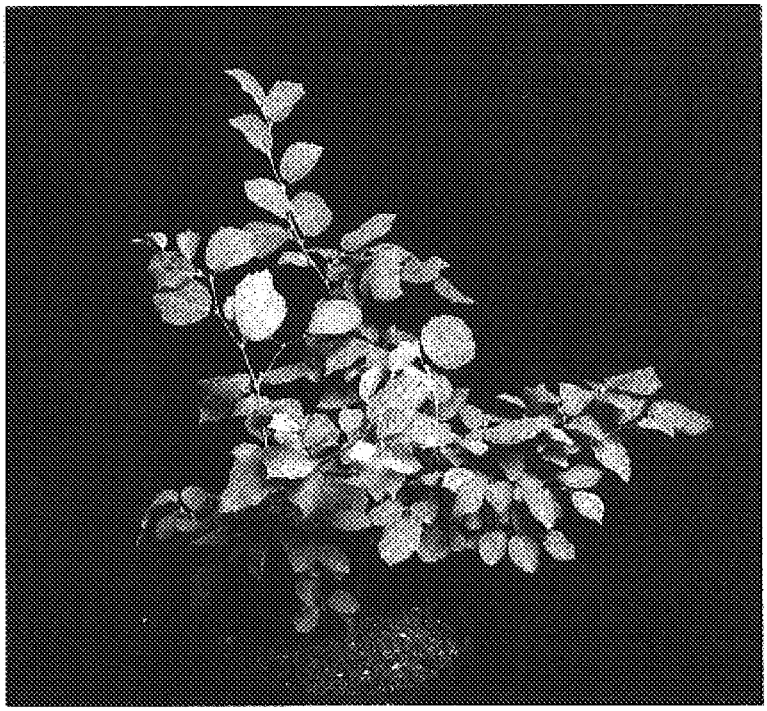
FIGS. 2 and 3 show the overall shape of the plant.
Figure 3:
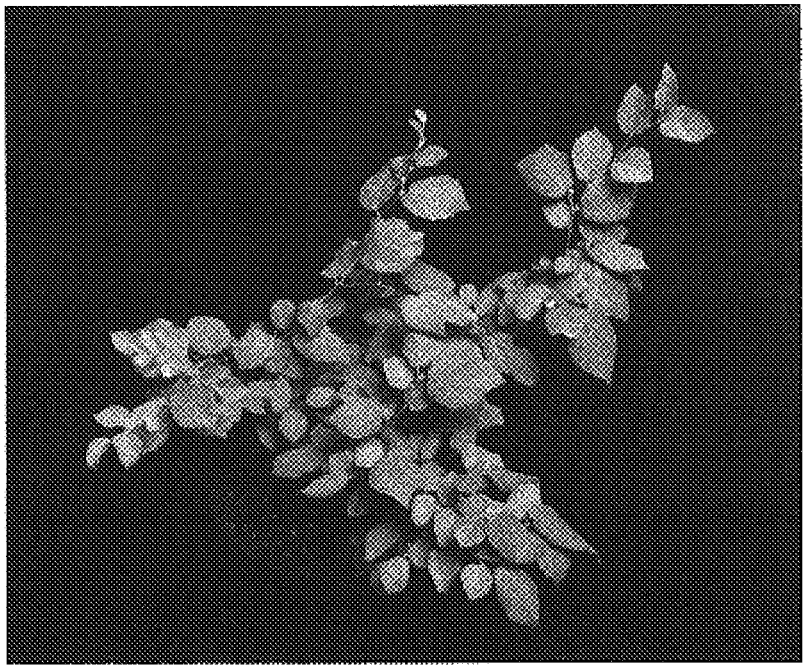

The following is a detailed description of the new cultivar based on observations of a three-year-old specimen grown in 3-gallon pots grown in shade with high nutrition in Boring, Oreg. The color descriptions are all based on The Royal Horticultural Society Colour Chart.

Plant:
- *Type.*—Deciduous shrub.
- *Hardiness.*—USDA Zones 4 to 9.
- *Size.*—Grows to 3 m high and wide.
- *Form.*—Globose.

Stem:
- *Type.*—Numerous, usually erect, same as *Fothergilla major* 'Mt. Airy'.
- *Size.*—Three-year stem is 1.3 cm wide.
- *Surface.*—Young branches are glaucous and have stellate pubescence.
- *Color from dormant plant.*—1 year old stem (wood that is formed in the current season) is Greyed Brown 199C. 2-year-old stem (wood that is formed in the last growing season) is Greyed Green 197C where least glaucous, and Greyed Green Group 188A, where most glaucous.

Dormant buds:
- *Size.*—Flower buds are 0.65 cm long and 0.5 cm wide. Leaf buds are 0.4 cm long and 0.2 cm wide.
- *Surface.*—Thick with stellate pubescence.
- *Color.*—Closest to 199C but somewhat pinker.

Leaf:
- *Type.*—Simple.
- *Shape.*—Broadly elliptic.
- *Arrangement.*—Alternate.
- *Length.*—4.5 to 7 cm.
- *Width.*—3.5 to 5.5 cm. at the widest part.
- *Vestiture.*—Stellate pubescent and glaucous.
- *Aspect.*—Matte.
- *Texture.*—Leathery.
- *Venation.*—Pinnate, main vein is sometimes pulled off center near the leaf tip due to leaf puckering.
- *Margins.*—Entire on lower ⅔, irregularly and coarsely serrate on top ⅓.
- *Apex.*—Obtuse.
- *Base.*—Oblique.
- *Petiole length.*—0.7 cm.
- *Petiole texture.*—Glaucous and stellate pubescent.
- *Petiole color.*—Yellow Green 147B (where least glaucous) to Greyed Brown 199D (where most glaucous).

*Stipules.*—Deciduous, ovate, 4 mm long and 3 mm wide, with stellate pubescence.

*Color.*—Topside — Greyed Green Group 188A, where least glaucous, and Black Group 202C, where most glaucous. New Growth — Closest to Greyed Green 189B. Spring new leaves and stipules — Closest to Green 138A. Bottom — Green Group 138A. Fall Color — Closest to Greyed Purple 186B.

Flower, fruit and seed: Flowers were observed in March of 2004. They bloomed at the same time as 'Mt. Airy' and looked identical. 'Mt. Airy' and 'Blue Shadow' flower in terminal spikes, 5 cm long and 5.2 cm wide, erect on short side branches, blooming with the new leaves. The flowers are bisexual, apetalous, and are composed of 20 to 36 attractive stamens. The filaments are 1.5 to 2 cm long and White 155D. The styles are also White 155D and are 11 mm long and thinner than the anthers. New flower buds are lime green, Yellow Green 144B. The anthers are light yellow, Yellow 9D. The pollen is Yellow 9B. The flowers are fragrant of honey with a slight licorice overtone. Observations of fruit and seed for 'Blue Shadow' have not been made.

COMPARISONS TO SIMILAR *FOTHERGILLA*

Compared to *Fothergilla major* 'Mt. Airy' (an unpatented plant), this new cultivar has a completely different leaf color and shape. Its leaves are a blue green rather than green. Its leaf shape is rounder. Because this new cultivar is so glaucous its surface is not glossy like *Fothergilla major* 'Mt. Airy'. This glaucous covering extends to the young branches making them a different color as well. Their habits, growth rate, and eventual size are the same. Both have excellent fall color.

I claim:

1. A new and distinct cultivar of *Fothergilla major* plant as shown and described, characterized by its striking glaucous, blue green leaf color.

* * * * *